US011707594B2

(12) United States Patent
Kuzelka et al.

(10) Patent No.: US 11,707,594 B2
(45) Date of Patent: Jul. 25, 2023

(54) SYSTEMS AND METHOD FOR AN OPTICAL ANESTHETIC AGENT LEVEL SENSOR

(71) Applicant: GE Precision Healthcare LLC, Milwaukee, WI (US)

(72) Inventors: Russell James Kuzelka, McFarland, WI (US); Tomi Tapani Pekkarinen, Espoo (FI)

(73) Assignee: GE Precision Healthcare LLC, Milwaukee, WI (US)

( * ) Notice: Subject to any disclaimer, the term of this patent is extended or adjusted under 35 U.S.C. 154(b) by 857 days.

(21) Appl. No.: 16/568,202

(22) Filed: Sep. 11, 2019

(65) Prior Publication Data

US 2021/0069455 A1    Mar. 11, 2021

(51) Int. Cl.
*A61M 16/18* (2006.01)
*A61M 16/20* (2006.01)
*A61M 16/00* (2006.01)

(52) U.S. Cl.
CPC ........ *A61M 16/18* (2013.01); *A61M 16/0003* (2014.02); *A61M 16/0057* (2013.01); *A61M 16/024* (2017.08); *A61M 16/208* (2013.01); *A61M 2016/003* (2013.01); *A61M 2205/3306* (2013.01); *A61M 2205/3334* (2013.01); *A61M 2205/3375* (2013.01); *A61M 2205/3386* (2013.01); *A61M 2205/581* (2013.01); *A61M 2205/583* (2013.01)

(58) Field of Classification Search
CPC .............. A61M 16/18; A61M 16/0003; A61M 16/024; A61M 16/0057; A61M 16/208; A61M 16/104; A61M 16/01; G01F 23/0038
See application file for complete search history.

(56) References Cited

U.S. PATENT DOCUMENTS

| 4,938,590 | A | * | 7/1990 | Ishida ................... G01F 23/686 73/306 |
| 5,291,031 | A | * | 3/1994 | MacDonald ............ G01F 23/68 250/577 |
| 5,824,885 | A | * | 10/1998 | Lekholm ............. A61M 16/209 73/440 |

(Continued)

FOREIGN PATENT DOCUMENTS

| CN | 201218744 Y | * | 4/2009 |
| JP | 2864776 B2 | * | 3/1999 |

(Continued)

*Primary Examiner* — Margaret M Luarca

(57) ABSTRACT

Systems and methods are provided for anesthetic agent level sensing. In one embodiment, a system for a level sensor for an anesthetic vaporizer includes a measurement tube including a float positioned therein, a bottom portion of the measurement tube coupled to a cap having a central opening, a retaining bracket coupled to a top portion of the measurement tube, an optical sensor housed within the retaining bracket, the optical sensor including a light source positioned to emit light toward an interior of the measurement tube and a light detector positioned to receive light from the interior of the measurement tube, and an optical window housed within the retaining bracket and coupled between the optical sensor and the interior of the measurement tube.

14 Claims, 6 Drawing Sheets

(56) References Cited

U.S. PATENT DOCUMENTS

| | | | | |
|---|---|---|---|---|
| 6,077,356 | A | * | 6/2000 | Bouchard ............ C23C 16/4482 |
| | | | | 222/61 |
| 7,121,140 | B2 | * | 10/2006 | Lo ............................ G01F 23/68 |
| | | | | 73/290 R |
| 7,287,557 | B2 | * | 10/2007 | Bunke .................... A61M 16/18 |
| | | | | 141/2 |
| 8,159,660 | B2 | | 4/2012 | Mimeault et al. |
| 9,797,764 | B2 | * | 10/2017 | Bluemner ............ A61M 16/024 |
| 2007/0181703 | A1 | * | 8/2007 | Buchanan ................ F22B 35/00 |
| | | | | 237/58 |
| 2018/0154443 | A1 | * | 6/2018 | Milshtein .............. B29C 64/393 |

FOREIGN PATENT DOCUMENTS

| | | | | |
|---|---|---|---|---|
| WO | WO-2008151667 | A1 | * 12/2008 | ........ A61M 16/0003 |
| WO | WO-2012094223 | A1 | * 7/2012 | .......... A61M 16/183 |

\* cited by examiner

SYSTEMS AND METHOD FOR AN OPTICAL ANESTHETIC AGENT LEVEL SENSOR

FIELD

Embodiments of the subject matter disclosed herein relate to anesthesia systems, and more particularly, to systems and methods for monitoring a level of anesthetic agent remaining in an anesthetic vaporizer.

BACKGROUND

During some medical procedures, such as surgical procedures, a patient may be placed under general anesthesia by administrating an anesthetic agent. In some examples, the anesthetic agent may be a volatile anesthetic agent that is administered to the patient via an anesthetic vaporizer. For example, the anesthetic vaporizer may induce and control vaporization of the volatile anesthetic agent from a liquid form. A carrier gas (e.g., a mixture of oxygen and fresh air) may flow into the vaporizer and blend (e.g., mix and converge) with the anesthetic agent vapors before flowing to the patient, where they may be introduced via inhalation, for example.

Conventional anesthetic vaporizers include a sump for storing the liquid anesthetic agent before it is vaporized and delivered to the patient for inhalation. An operator (e.g., an anesthesiologist or other clinician) may monitor a level of liquid anesthetic agent in the sump, both before use and during use, to ensure sufficient anesthetic agent is available for delivery to the patient during the medical procedure.

BRIEF DESCRIPTION

In one embodiment, a system for a level sensor for an anesthetic vaporizer includes a measurement tube including a float positioned therein, a bottom portion of the measurement tube coupled to a cap having a central opening, a retaining bracket coupled to a top portion of the measurement tube, an optical sensor housed within the retaining bracket, the optical sensor including a light source positioned to emit light toward an interior of the measurement tube and a light detector positioned to receive light from the interior of the measurement tube, and an optical window housed within the retaining bracket and coupled between the optical sensor and the interior of the measurement tube. In this way, the level sensor may provide anesthetic agent level measurements with increased accuracy.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
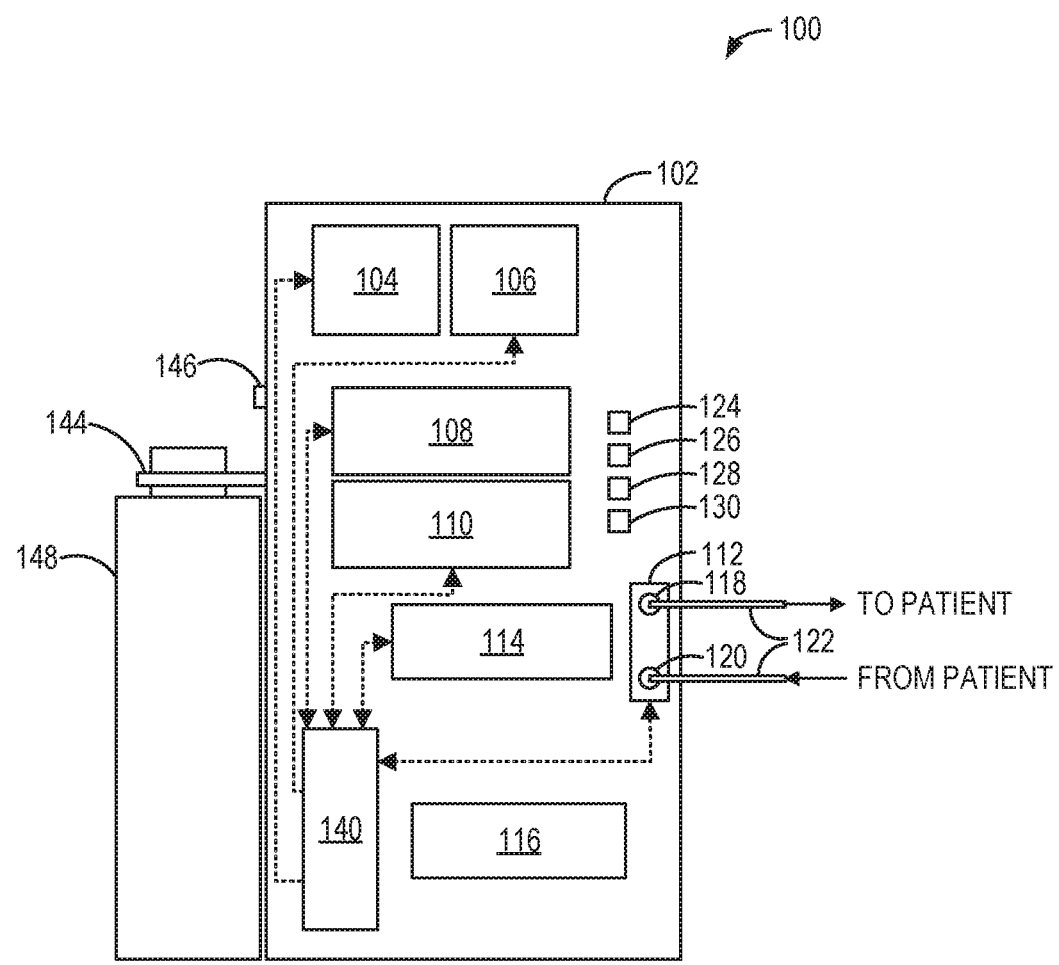
FIG. 1 schematically shows an exemplary embodiment of an anesthesia machine.

The following description relates to various embodiments for measuring and monitoring a level of liquid anesthetic agent in an anesthetic vaporizer, which may be included in an anesthesia machine. Currently available anesthetic agent level sensors, such as capacitive, acoustic/ultrasonic, and differential hydrostatic level sensors, may be affected by characteristics of the liquid anesthetic agent. For example, liquid anesthetic agents are halogenated solvents that may aggressively react with certain materials and/or deposit residues, such as a film composed of butylated hydroxytoluene (BHT), over time. As one example, changes to dielectric properties of the liquid anesthetic agent caused by BHT deposition over time may affect measurements made by capacitive level sensors. As another example, acoustic/ultrasonic level sensors may be impacted by changes in humidity and a temperature of the liquid anesthetic agent. As still another example, differential hydrostatic level sensors may be incompatible with the reactive anesthetic agents. As a result, the above-mentioned sensors may be unable to accurately measure anesthetic agent level, and therefore volume, across time and conditions.

Thus, according to embodiments disclosed herein, a level sensor is provided that is not affected by changes in in the characteristics of the liquid anesthetic agent. In the embodiments disclosed herein, the level sensor is coupled in a sump storing liquid anesthetic agent and includes a measurement tube and a float positioned therein. According to embodiments disclosed herein, the float vertically moves within the measurement tube and sits at a surface of the liquid anesthetic agent. In the embodiments disclosed herein, the level sensor includes an optical sensor including a light source positioned to emit light toward the float within the measurement tube and a light detector positioned to receive light reflected by the float. Further, the optical sensor may be coupled to an electronic controller, which may receive a signal output from the optical sensor corresponding to a distance between the float and the optical sensor, and the controller may use the signal output to determine a volume of liquid anesthetic agent remaining in the sump as well as a time-to-empty. In some embodiments, the controller may output a refill alert responsive to the time-to-empty decreasing below a threshold duration.

The embodiments disclosed herein may provide several advantages. For example, the optical sensor may measure a physical distance between the float and the sensor, which is not sensitive to physical characteristics of the liquid anesthetic agent, increasing an accuracy of the measurements made by the optical sensor. Further, the physical distance reproducibly relates to a calculable volume of the liquid anesthetic agent, enabling higher accuracy volume calculation. As another example, the embodiments disclosed herein provide a level sensor with a small form-factor that is agent compatible. Further, by determining the time-to-empty and outputting the refill alert, it may be ensured that sufficient anesthetic agent is available for delivery to a patient during a medical procedure without an operator of the anesthetic vaporizer having to closely monitor the liquid level, freeing the operator to focus on patient monitoring, for example.

Figure 2:
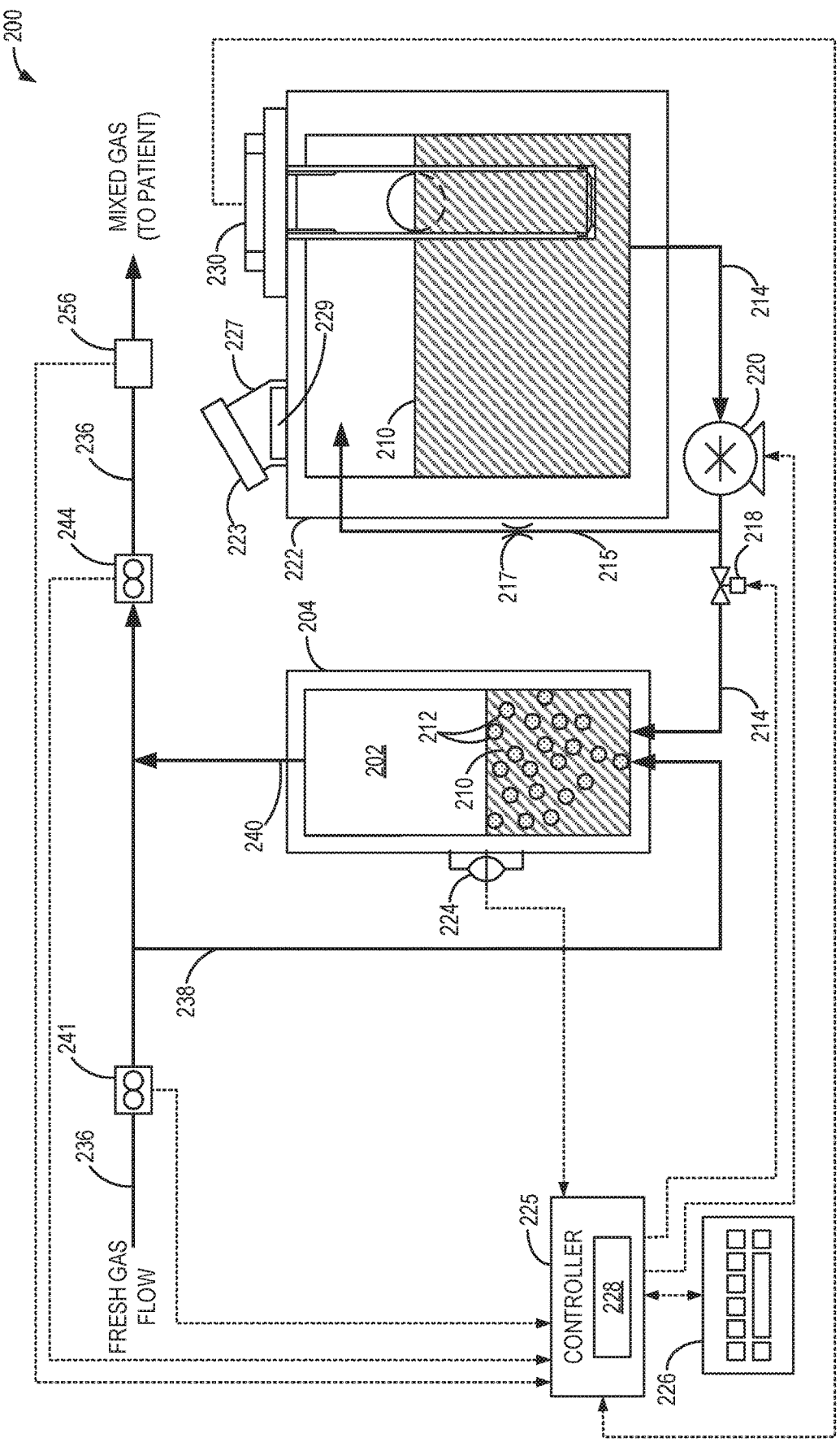
FIG. 2 schematically shows an exemplary embodiment of an anesthetic vaporizer that may be included in an anesthesia machine.
Figure 3:
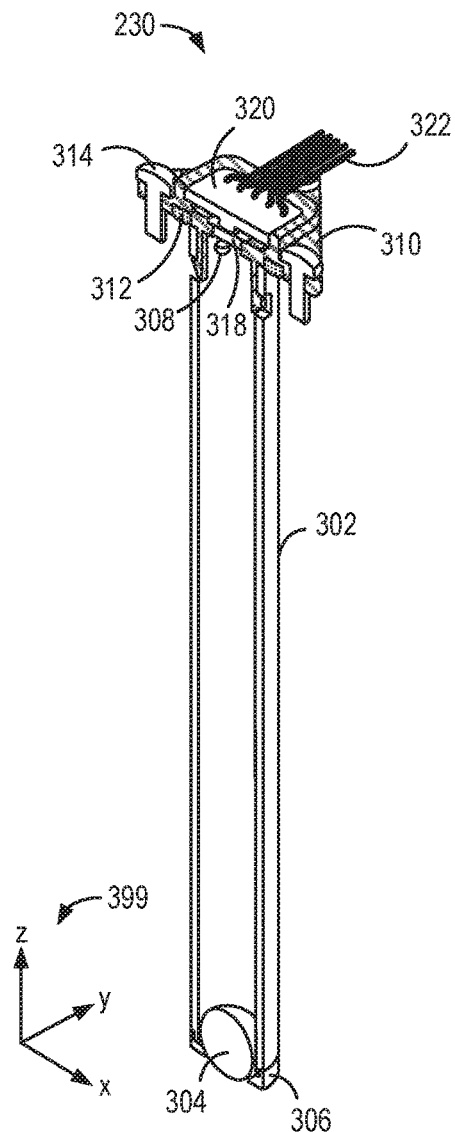
FIG. 3 shows a top perspective sectional view of an exemplary embodiment of an optical level sensor that may be coupled in a sump of an anesthetic vaporizer.
Figure 4:
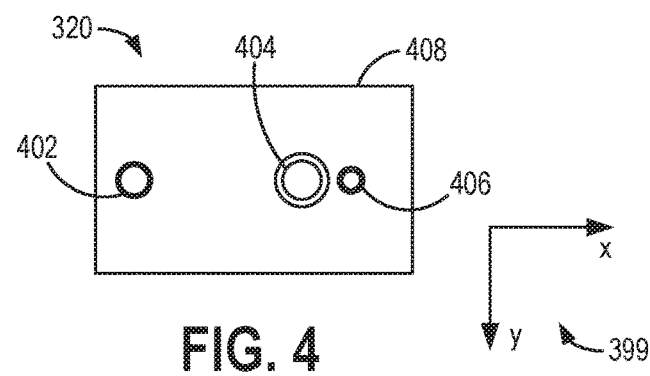
FIG. 4 shows an exemplary embodiment of a time-of-flight proximity sensor that may be included in an optical level sensor for determining an anesthetic agent volume.
Figure 6:
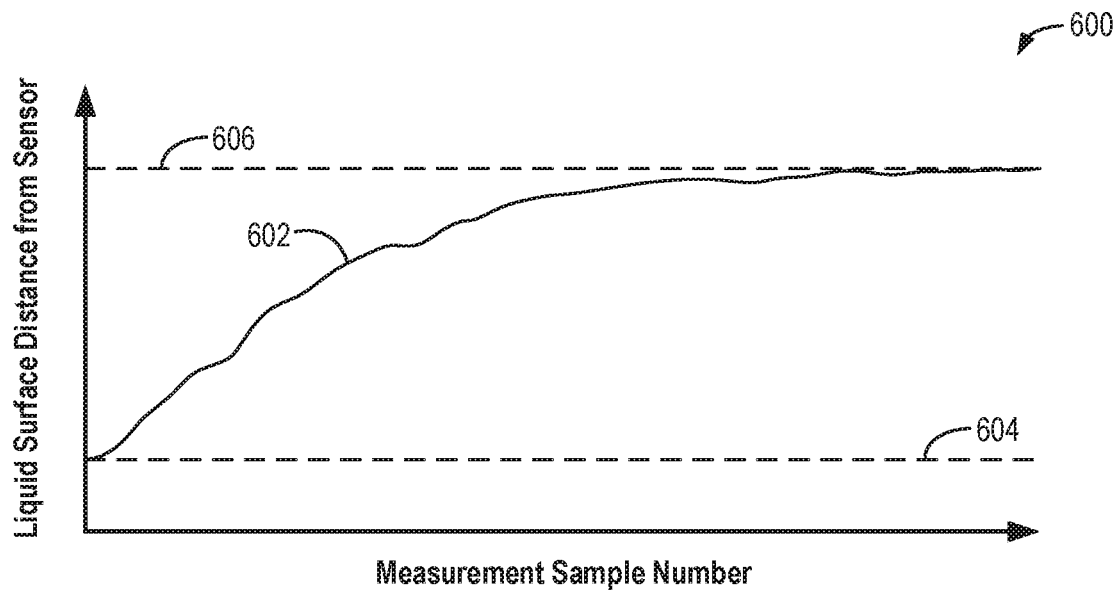
FIG. 6 depicts an example graph showing a continuous measurement of a distance to a surface of a liquid anesthetic agent made by a time-of-flight proximity sensor included in an optical level sensor.
Figure 7:
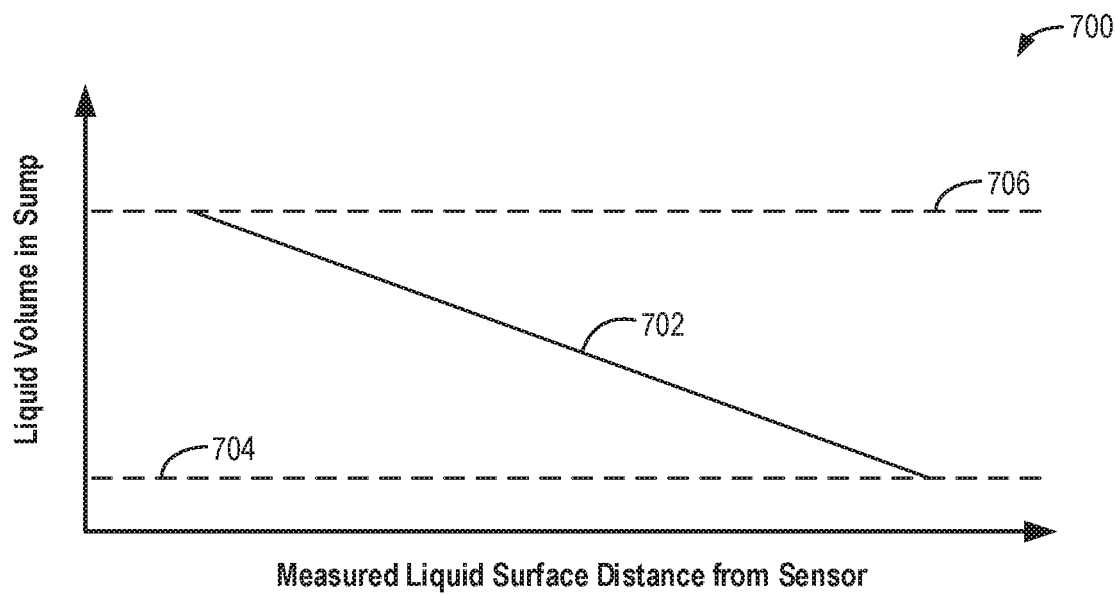
FIG. 7 shows an example graph of a relationship between a measured distance to a surface of a liquid anesthetic agent in a sump and a volume of the liquid anesthetic agent in the sump.
Figure 8:
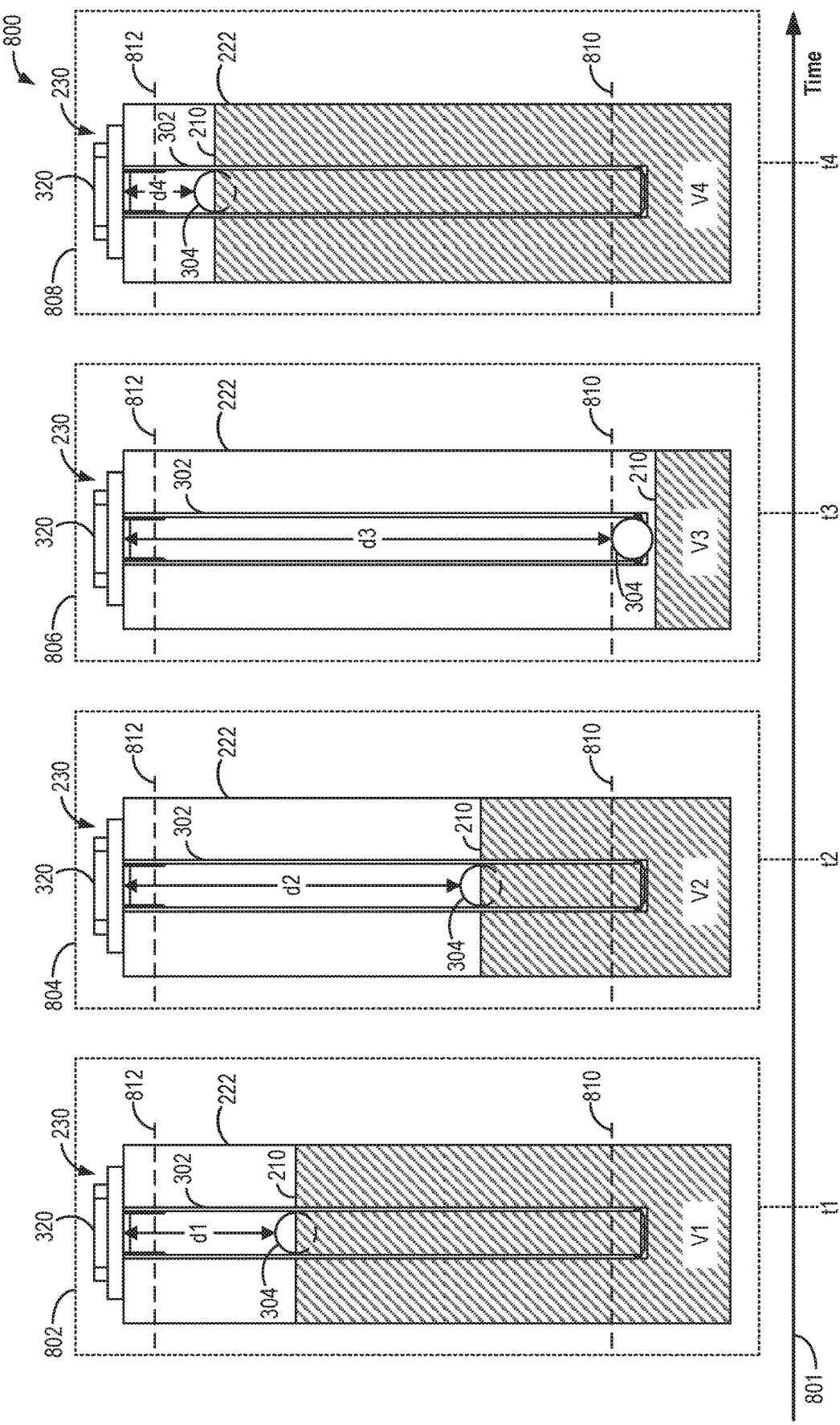
FIG. 8 schematically shows an example timeline for determining a volume of liquid anesthetic agent in a sump via an optical level sensor.

FIG. 1 schematically shows an exemplary embodiment of an anesthesia machine. FIG. 2 shows an exemplary embodiment of an anesthetic vaporizer that may be included in the anesthesia machine of FIG. 1. FIG. 3 shows a sectional view of an exemplary embodiment of a level sensor that may be coupled in a sump of the anesthetic vaporizer of FIG. 2. The level sensor may include at least one light source and at least one light detector, as shown in FIG. 4, and may measure a distance from the level sensor to a float on a surface of liquid anesthetic agent based on light reflections by the float, as diagrammed in FIG. 5. FIG. 6 depicts an example graph of how the measured distance may change over time as the sump is emptied, and FIG. 7 shows an example graph of a relationship between the measured distance and a volume of liquid anesthetic agent in the sump. FIG. 8 shows an example timeline showing how a level of the float, and a corresponding distance measured by the level sensor, changes as the level (and volume) of liquid anesthetic agent in the sump changes. A controller may track the volume of liquid anesthetic agent in the sump during use and alert an operator to refill the sump when a remaining operational time is low, such as according to the example method of FIG. 9. Likewise, depending on a current fresh gas flow rate and output agent concentration, the controller may calculate and display an instantaneous "time-to-empty".

FIG. 1 schematically shows an example anesthesia machine 100. Anesthesia machine 100 includes a frame (or housing) 102. In some embodiments, frame 102 may be supported by casters, where the movement of the casters may be controlled (e.g., stopped) by one or more locks. In some examples, the frame 102 may be formed of a plastic material (e.g., polypropylene). In other examples, the frame 102 may be formed of a different type of material (e.g., metal, such as steel).

Anesthesia machine 100 also includes an anesthesia display device 104, a patient monitoring display device 106, a respiratory gas module 108, one or more patient monitoring modules, such as a patient monitoring module 110, a ventilator 112 (explained in more detail below), an anesthetic vaporizer 114, and an anesthetic agent storage bay 116. Anesthesia machine 100 may further include a main power indicator 124, a system activation switch 126 (which, in one example, permits gas flow when activated), an oxygen flush button 128, and an oxygen control 130. An example embodiment of anesthetic vaporizer 114 will be described below with respect to FIG. 2. Anesthetic vaporizer 114 may vaporize the anesthetic agent and combine the vaporized anesthetic agent with one or more medical grade gases (e.g., oxygen, air, nitrous oxide, or combinations thereof), which may then be delivered to a patient.

Anesthesia machine 100 may additionally include an integrated suction, an auxiliary oxygen flow control, and various other components for providing and/or controlling a flow of the one or more medical grade gases to the patient. For example, anesthesia machine 100 includes one or more pipeline connections 146 to facilitate coupling of the anesthesia machine to pipeline gas sources. Additionally, anesthesia machine 100 includes a cylinder yoke 144, via which one or more gas-holding cylinders 148 may be coupled to the anesthesia machine. Thus, through the pipeline connection and/or cylinder connections, gas may be provided to the anesthesia machine, where the gas may include (but is not limited to) medical air, oxygen, nitrogen, and nitrous oxide. The gas that enters the anesthesia machine may mix with the vaporized anesthetic agent at the anesthetic vaporizer 114, as described above, before being supplied to a patient via the ventilator 112. The anesthesia machine may also include a serial port, a collection bottle connection, a cylinder wrench storage area, and an anesthesia gas scavenging system.

The ventilator 112 may include an expiratory check valve at an expiratory port 120, an expiratory flow sensor at the expiratory port 120, an inspiratory check valve at an inspiratory port 118, an inspiratory flow sensor at the inspiratory port 118, an absorber canister, a manual bag port, a ventilator release, an adjustable pressure-limiting valve, a bag/vent switch, and a bellows assembly. When a patient breathing circuit is coupled to the ventilator 112, breathing gases (e.g., air, oxygen, and/or nitrous oxide mixed with vaporized anesthetic agent) exit the anesthesia machine from the inspiratory port 118 and travel to the patient. Expiratory gases from the patient re-enter the anesthesia machine via the expiratory port 120, where carbon dioxide may be removed from the expiratory gases via the absorber canister.

During operation of the anesthetic vaporizer 114, an operator (e.g., an anesthesiologist) may adjust an amount of vaporized anesthetic agent that is supplied to the patient by adjusting a flow rate of gases from the gas source(s) (e.g., the pipeline gas supply) to the vaporizer. The flow rate of the gases from the gas source to the vaporizer may be adjusted by the operator via adjustment of one or more flow adjustment devices. For example, the flow adjustment devices may include analog and/or digital adjustment dials and/or other user input devices configured to actuate one or more flow control valves of anesthesia machine 100. In some embodiments, a first flow control valve may be positioned between the gas source(s) and the anesthetic vaporizer 114 and may be actuatable via the flow adjustment devices to a fully opened position, a fully closed position, and a plurality of positions between the fully opened position and the fully closed position.

Anesthesia machine 100 may additionally include one or more valves configured to bypass gases from the gas source(s) around the anesthetic vaporizer 114. The valves may enable a first portion of gases to flow directly from the gas source to the inspiratory port 118 and a second portion of gases to flow from the gas source through the anesthetic vaporizer 114 to mix with the vaporized anesthetic agents prior to flowing to the inspiratory port 118. By adjusting a ratio of the first portion of gases relative to the second portion of gases, the operator may control a concentration of vaporized anesthetic agent administered to the patient via the inspiratory port 118.

Further, the adjustments described above may be facilitated at least in part based on output from the respiratory gas module 108. The respiratory gas module 108 may be configured to measure various parameters of the gases exiting the vaporizer and/or being provided to the patient. For example, the respiratory gas module 108 may measure the concentrations of carbon dioxide, nitrous oxide, and the anesthetic agent provided to the patient. Further, the respiratory gas module 108 may measure respiration rate, minimum alveolar concentration, patient oxygen, and/or other parameters. The output from the respiratory gas module 108 may be displayed via a graphical user interface on a display device (e.g., the anesthesia display device 104 and/or the patient monitoring display device 106) and/or used by a controller to provide closed-loop feedback control of the amount of anesthesia provided to the patient.

The ventilator 112 may optionally be coupled to a breathing circuit (not shown) including a plurality of tubes (e.g., gas passages) 122. The breathing circuit may be coupled between an airway of a patient (e.g., via a breathing mask positioned to enclose the mouth and/or nose of the patient or a tracheal intubation tube) and the inspiratory port 118. Gases (e.g., the one or more medical gases, or a mixture of the one or more medical gases and vaporized anesthetic agent from the anesthetic vaporizer 114) may flow from the inspiratory port 118, through the breathing circuit, and into the airway of the patient, where the gases are absorbed by the lungs of the patient. By adjusting the concentration of vaporized anesthetic agent in the gases as described above, the operator may adjust a degree to which the patient is anesthetized.

During conditions in which the breathing circuit is coupled to the airway, the anesthetic agent and/or fresh gas (without the anesthetic agent) may flow into the airway of the patient (e.g., through inhalation) via the inspiratory port 118 and the inspiratory check valve. As an example, the inspiratory check valve may open automatically (e.g., without input or adjustment by the operator) in response to inhalation by the patient and may close automatically in response to exhalation by the patient. Similarly, the expiratory check valve may open automatically in response to exhalation by the patient and may close automatically in response to inhalation by the patient.

In some embodiments, the operator may additionally or alternatively control one or more operating parameters of the anesthesia machine 100 via an electronic controller 140 of the anesthesia machine 100. Controller 140 includes a processor operatively connected to a memory. The memory may be a non-transitory computer-readable medium and may be configured to store computer executable code (e.g., instructions) to be processed by the processor in order to execute one or more routines, such as those described herein. The memory may also be configured to store data received by the processor. Controller 140 may be communicatively coupled (e.g., via wired or wireless connections) to one or more external or remote computing devices, such as a hospital computing system, and may be configured to send and receive various information, such as electronic medical record information, procedure information, and so forth. Controller 140 may also be electronically coupled to various other components of the anesthesia machine 100, such as the anesthetic vaporizer 114, the ventilator 112, the respiratory gas module 108, the anesthesia display device 104, and the patient monitoring display device 106.

The controller 140 receives signals from the various sensors of the anesthesia machine 100 and employs the various actuators of the anesthesia machine 100 to adjust operation of the anesthesia machine 100 based on the received signals and instructions stored on the memory of the controller. For example, the flow of gases to the inspiratory port 118 may be controlled via an input device (e.g., keyboard, touchscreen, etc.) coupled to the electronic controller of the anesthesia machine 100. The controller 140 may display operating parameters of the anesthesia machine 100 via the anesthesia display device 104 and/or the patient monitoring display device 106. The controller may receive signals (e.g., electrical signals) via the input device and may adjust operating parameters of the anesthesia machine 100 in response (e.g., responsive) to the received signals.

As one example, the operator may input a desired concentration of the anesthetic agent to be delivered to the patient. A corresponding valve position of one or more valves of the anesthesia machine (e.g., a position of one or more bypass valves, as described above) may be empirically determined and stored in a predetermined lookup table or function in a memory of the controller. For example, the controller may receive the desired concentration of the anesthetic agent via the input device and may determine an amount of opening of the one or more valves corresponding to the desired concentration of the anesthetic agent based on the lookup table, with the input being the concentration of the anesthetic agent and the output being the valve position of the one or more valves. The controller may transmit an electrical signal to an actuator of the one or more valves in order to adjust each of the one or more valves to the corresponding output valve position. In some examples, the controller may compare the desired flow rate of gases to a measured flow rate of gases, such as measured by the inspiratory flow sensor, for example.

Controller 140 is shown in FIG. 1 for illustrative purposes, and it is to be understood that controller 140 may be located in various locations within, around, and/or remote from anesthesia machine 100. As an example, controller 140 may include multiple devices/modules that may be distributed throughout anesthesia machine 100. As such, controller 140 may include a plurality of controllers at various locations within anesthesia machine 100. As another example, additionally or alternatively, controller 140 may include one or more devices/modules that are external to anesthesia machine 100, located proximate to (e.g., in a same room) or remote from (e.g., a remote server) anesthesia machine 100. In each example, the multiple devices/modules may be communicatively coupled through wired and/or wireless connections.

Anesthetic vaporizers, such as anesthetic vaporizer 114 shown in FIG. 1, may employ various methods to vaporize a liquid anesthetic agent. For example, the anesthetic vaporizer may use a flow-over method (in which a carrier gas flows over a top surface of a volatile liquid anesthetic agent), a bubble-through method (in which the carrier gas is bubbled up through the liquid anesthetic agent), or a gas/vapor blender (in which heat is used to vaporize the liquid anesthetic agent, and the vapors are injected into a fresh gas flow). Regardless of the vaporization method, in some embodiments, the anesthetic vaporizer 114 may include a sump for storing the liquid anesthetic agent before it is delivered to a vaporizing chamber.

FIG. 2 shows an exemplary embodiment of an anesthetic vaporizer 200, which may be included in an anesthesia machine (e.g., anesthesia machine 100 shown in FIG. 1). As one example, anesthetic vaporizer 200 may be anesthetic vaporizer 114 of FIG. 1. In the embodiment shown in FIG. 2, anesthetic vaporizer 200 is a bubble-through anesthetic vaporizer, including a vaporizing chamber 202 defined by a housing 204. However, in other embodiments, anesthetic vaporizer 200 may be another type of anesthetic vaporizer (e.g., draw over, injector-based, wick-based, etc.) for use with a volatile liquid anesthetic agent that includes a controller and level sensing technology.

A lower portion of vaporizing chamber 202 is shown holding a liquid anesthetic agent 210 that is supplied from a sump 222 via a conduit 214 and a pump 220. The liquid anesthetic agent 210 may be isoflurane, sevoflurane, or another liquid anesthetic agent of similar volatility, for example, that is stored in sump 222. Pump 220 may be a positive displacement pump, such as a reciprocating positive displacement pump, for example. Pump 220 may be selectively operated to deliver liquid anesthetic agent 210 from sump 222 to vaporizing chamber 202 in response to a command signal from a controller 225, as will be further described below. Controller 225 may be an electronic controller including a processor operatively connected to a memory 228. Controller 225 may be included in (e.g., a part of) or communicatively coupled to controller 140 shown in FIG. 1, for example.

Sump 222 may be refilled via a fill cap 223 and a filler port (e.g., neck) 227 having an inlet filler port valve 229 positioned therein. Together, fill cap 223, filler port 227, and inlet filler port valve 229 may be included in a fill assembly. For example, an operator of anesthetic vaporizer 200 may remove fill cap 223 to refill sump 222 with additional liquid anesthetic agent 210 (e.g., from a refill bottle) via filler port 227 and inlet filler port valve 229 and then replace fill cap 223 to seal sump 222. Fill cap 223 may be a screw cap, for example. In some embodiments, inlet filler port valve 229 may be a mechanically actuated spring-loaded valve that opens when the refill bottle is attached to filler port 227 to enable liquid anesthetic agent 210 to flow from the refill bottle to the interior of sump 222 and closes when the refill bottle is not attached to filler port 227. Additionally or alternatively, in some embodiments, inlet filler port valve 229 may be an electronically actuated valve that may be adjusted in response to a control signal received from controller 225, as will be further described below. Thus, in some embodiments, inlet filler port valve 229 may be both mechanically and electronically actuated. Thus, sump 222 may be a sealed system when fill cap 223 is in place.

Conduit 214 may further include a shut-off valve 218 coupled between pump 220 and vaporizing chamber 202. For example, shut-off valve 218 may be an on-off valve, wherein shut-off valve 218 is actuated to an open (e.g., fully open) position that allows liquid anesthetic agent 210 to flow between and pump 220 and vaporizing chamber 202 or a closed (e.g., fully closed) position that prevents (e.g., blocks) the flow of liquid anesthetic agent 210 between pump 220 and vaporizing chamber 202. Shut-off valve 218 may be actuated between the open and closed positions in response to a command signal from controller 225, for example. A liquid return line 215 may be coupled to conduit 214 between shut-off valve 218 and pump 220 to reduce pressure build up between shut-off valve 218 and pump 220, such as when shut-off valve 218 is closed. For example, excess liquid anesthetic agent 210 provided by pump 220 may be returned to sump 222 via liquid return line 215. Further, liquid return line 215 may include a restriction 217, such as an orifice, to control flow through liquid return line 215 such that liquid anesthetic agent 210 preferentially flows through shut-off valve 218 instead of restriction 217 when shut-off valve 218 is open.

Controller 225 may selectively activate pump 220 to provide liquid anesthetic agent 210 from sump 222 to vaporizing chamber 202. In one embodiment, controller 225 may adjust operation of pump 220 responsive to a measurement received from a level sensor 224. For example, level sensor 224 may be any type of liquid level sensor, such as an optical, ultrasonic, capacitive, float, or pressure-based liquid level sensor positioned to measure a level of liquid anesthetic agent 210 in vaporizing chamber 202. As one example, controller 225 may be configured to maintain the level of liquid anesthetic agent at a target level or within a target range in order to prevent both underfilling and overfilling of vaporizing chamber 202.

In some embodiments, pump 220 may include a positive displacement stepper motor, where each positive displacement step of the pump is equivalent to a specified volume of liquid anesthetic agent 210. In this manner, the pump can be used to precisely fill the vaporizing chamber 202 and prevent overfill by recording the number of pump steps delivered. This approach may also be used to record a volume of anesthetic agent delivered to vaporizing chamber 202, which may be valuable for vaporizer run-time/maintenance analysis (service metrics), liquid leak detection, precise determination of an amount of liquid anesthetic remaining and available for delivery, vaporization efficiency calculations, etc.

Anesthetic vaporizer 200 includes an additional level sensor 230 positioned to measure a level of liquid anesthetic agent 210 in sump 222. In the embodiment shown in FIG. 2, level sensor 230 includes an optical time-of-flight (ToF) proximity sensor, components of which will be detailed below with respect to FIGS. 3 and 4. Level sensor 230 serves as a continuous liquid level sensor that is not affected by changes in operating conditions (e.g., temperature and humidity) or changes in liquid anesthetic agent 210 itself (e.g., dielectric constant). As will be further described below with particular respect to FIGS. 5-9, output from level sensor 230 may be used to determine a volume (e.g., amount) of liquid anesthetic agent 210 remaining in sump 222 as well as a duration of time remaining until refilling of sump 222 is indicated. As shown in the embodiment of FIG. 2, level sensor 230 may be coupled to a top exterior surface of sump 222 and extend into an interior of sump 222. For example, an elongated portion of level sensor 230 may extend through an opening in a housing of sump 222, while the external portion of level sensor 230 may form a gas-tight seal with sump 222. This configuration may enable level sensor 230 to perform top-down measurements through a vapor space above a surface of liquid anesthetic agent 210, for example. Further, in the exemplary embodiment of anesthetic vaporizer 200, level sensor 230 does not touch a bottom interior surface of sump 222, although a distance between the bottom-most surface of level sensor 230 and the bottom interior surface of sump 222 may vary. As will be elaborated herein, the distance between the bottom-most surface of level sensor 230 and the bottom interior surface of sump 222 results in a volume of liquid anesthetic agent 210 that is not measured by level sensor 230 as an additional reserve to help prevent complete emptying of sump 222. Further, controller 225 may track the level (or volume) of liquid anesthetic agent 210 in sump 222 during refilling via measurements received from level sensor 230. In embodiments where inlet filler port valve 229 is electronically actuated, controller 225 may actuate inlet filler port valve 229 closed responsive to the measured level (or volume) reaching a maximum level (or volume) to prevent inadvertent overfilling/overflowing of sump 222.

An upper portion of vaporizing chamber 202 (e.g., above a surface of liquid anesthetic agent 210) holds vapor, which may be a mixture of vaporized anesthetic agent and a carrier gas from a fresh gas flow. The fresh gas flow, and thus the carrier gas, may include one or more medical grade gases, such as oxygen, air, nitrous oxide, and combinations thereof. The fresh gas flow may be provided via one or more gas pipelines (e.g., via pipeline connections 146 shown in FIG. 1) and/or one or more gas-holding cylinders (e.g., gas-holding cylinder 148 of FIG. 1). As shown in FIG. 2, the fresh gas flow may enter anesthetic vaporizer 200 via a first gas passage 236. A first mass flow sensor 241 may be coupled to first gas passage 236 to measure a flow rate of the fresh gas flow entering anesthetic vaporizer 200. For example, first mass flow sensor 241 may be an ultrasonic flow meter or a calorimetric (thermal) mass flow meter.

In the exemplary embodiment of FIG. 2, a second gas passage 238 branches off from first gas passage 236 downstream of first mass flow sensor 241 to provide carrier gas to vaporizing chamber 202. As used herein, "carrier gas" refers to a portion of the fresh gas flow that flows to vaporizing chamber 202, whereas "bypass gas" refers to a remaining portion of the fresh gas flow that does not flow through vaporizing chamber 202, as will be elaborated below. For example, second gas passage 238 may pass through an opening in housing 204, which may include a gas-tight seal, to flow the carrier gas through a bottom of vaporizing chamber 202. However, in other embodiments, anesthetic vaporizer 200 may not include second gas passage 238, and carrier gas may not be delivered to vaporizing chamber 202. For example, carrier gas may not be delivered to vaporizing chamber 202 when the liquid anesthetic agent 210 has a relatively low boiling point (e.g., at or around room temperature), such as when liquid anesthetic agent 210 is desflurane or another liquid anesthetic agent of similar volatility. Additionally or alternatively, second gas passage 238 may not be included in embodiments where a different type of anesthetic vaporizer architecture is used (e.g., a flow over type or a gas/vapor blender). Thus, the embodiment shown in FIG. 2 is provided by way of example.

The carrier gas delivered to vaporizing chamber 202 via second gas passage 238 flows through liquid anesthetic agent 210 to form a plurality of gas bubbles 212. The plurality of gas bubbles 212 pass through liquid anesthetic agent 210, becoming saturated with vaporized anesthetic agent, as they rise to the surface of the liquid. In some examples, a heating element may be coupled to or within vaporizing chamber 202 to increase a temperature of liquid anesthetic agent 210 and provide energy for vaporization (e.g., latent heat of vaporization).

Vapor, such as the carrier gas that is saturated with vaporized anesthetic agent, may flow out of vaporizing chamber 202 via a third gas passage 240 (e.g., a vapor delivery passage). For example, third gas passage 240 may pass through an opening at or near a top of housing 204 and form a junction with first gas passage 236 to fluidically couple the upper portion of vaporizing chamber 202 with first gas passage 236. Upstream of the junction with third gas passage 240 and downstream of the junction with second gas passage 238, first gas passage 236 carries the bypass gas portion of the fresh gas flow. The bypass gas does not pass through vaporizing chamber 202. The bypass gas, containing no vaporized anesthetic agent, and the vapor from vaporizing chamber 202, containing the carrier gas saturated with the vaporized anesthetic agent, mix at and downstream of the junction between first gas passage 236 and third gas passage 240. The mixed gas may then be delivered to the patient via an inspiratory limb of a breathing circuit (e.g., via inspiratory port 118 described with respect to FIG. 1). A second mass flow sensor 244 may be coupled to first gas passage 236 downstream of the junction with third gas passage 240 to measure a flow rate of the mixed gas exiting anesthetic vaporizer 200. For example, second mass flow sensor 244 may be an ultrasonic flow meter or a calorimetric mass flow meter. In the case of an ultrasonic flow metering architecture, the output anesthetic agent concentration may be calculated by the difference in the measured time-of-flight between upstream ultrasonic flow sensor 241 and downstream ultrasonic flow sensor 244.

In some embodiments, an independent concentration sensor 256 may be coupled to first gas passage 236 downstream of the junction with third gas passage 240. Concentration sensor 256 may be any suitable sensor that is configured to measure a concentration of the anesthetic agent in the mixed gas. As one example, concentration sensor 256 may be an optical sensor that transmits light of a suitable wavelength (e.g., infrared) through the mixed gas and determines a concentration of the anesthetic agent based on an absorption of the light by the mixed gas. In other examples, the concentration sensor may be a carbon dioxide or oxygen sensor that measures the concentration of the anesthetic agent based on a displacement of the carbon dioxide or oxygen relative to a supplied concentration of carbon dioxide or oxygen in the fresh gas flow. Concentration sensor 256 may output a signal to controller 225 indicative of the measured concentration of the anesthetic agent (e.g., the concentration of the anesthetic agent vapor) in the mixed gas.

In addition to receiving signals output by level sensor 224, level sensor 230, concentration sensor 256, first mass flow sensor 241, and second mass flow sensor 244, controller 225 may receive additional signals, including signals from one or more pressure and temperature sensors coupled in various locations throughout anesthetic vaporizer 200. Controller 225 receives the signals from the various sensors of FIG. 2, processes the input data, and employs the various actuators of FIG. 2 to adjust operation of anesthetic vaporizer 200 based on the received signals and instructions stored on a memory of the controller. For example, controller 225 may receive a measurement from level sensor 230 and determine a volume of liquid anesthetic agent 210 remaining in sump 222 based on the received measurement, as will be described below with respect to FIG. 9. Additionally, the controller may output an alert to the operator via a human-machine interface (HMI) 226 that is operationally connected to the controller (e.g., via wired or wireless communication) responsive to a refill indication. Further, data may be input to controller 225 by the operator of anesthetic vaporizer 200 via HMI 226. Thus, HMI 226 may include both a user input device and an output device. The user input device may include one or more of a mouse, a keyboard, a voice input device, a touch input device for receiving a gesture from the operator, a motion input device for detecting non-touch gestures and other motions by the operator, and other comparable input devices, as well as associated processing elements capable of receiving user input from the operator. The output device may include one or more of a display (e.g., anesthesia display device 104 and/or patient monitoring display device 106 of FIG. 1) for providing visual alerts or text-based messages and a speaker for providing audible alerts or messages.

Turning now to FIG. 3, a top perspective sectional view of level sensor 230 introduced in FIG. 2 is shown. Specifically, FIG. 3 shows an example configuration of level sensor 230 with relative positioning of the various components. If shown directly contacting each other, or directly coupled, then such elements may be referred to as directly contacting or directly coupled, respectively, at least in one embodiment. Similarly, elements shown contiguous or adjacent to one another may be contiguous or adjacent to each other, respectively, at least in one embodiment. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a top-most element or point of element may be referred to as a "top" of the component and a bottom-most element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example. Additionally, reference axes 399 are provided to describe the relative arrangement of components. Reference axes 399 includes the z-axis as the vertical axis, with the z-axis increasing from bottom to top (e.g., in the direction of the z-axis arrow). The top-most point has the greatest z-axis value and is also the top-most point with respect to gravity.

Level sensor 230 includes a measurement tube 302 with a float 304 positioned therein. Measurement tube 302 is shaped as an elongated hollow cylinder (e.g., extending in the vertical direction) having an inner diameter and an outer diameter, the outer diameter and the inner diameter separated by a wall thickness of the measurement tube. Float 304 is shaped as a sphere having an outer diameter that is smaller than the inner diameter of measurement tube 302. Because the outer diameter of float 304 is less than the inner diameter of measurement tube 302, float 304 may move freely along a length of measurement tube 302 (e.g., in the vertical z-direction) between an upper bound and a lower bound, as will be elaborated below. Further, the difference between the outer diameter of float 304 and the inner diameter of measurement tube 302 may be small, such that float 304 does not appreciably translate within measurement tube 302 in the (horizontal) x- and y-directions.

Measurement tube 302 and float 304 may each be comprised of one or more anesthetic agent-compatible (e.g., non-reactive) materials. Further, measurement tube 302, particularly an inner surface of measurement tube 302, may be comprised of a smooth, anti-reflective material. In one exemplary embodiment, measurement tube 302 is comprised of aluminum and includes black nickel plating on the inner surface. In another exemplary embodiment, measurement tube 302 is comprised of black extruded polypropylene. In still another embodiment, measurement tube 302 is comprised of opaque high density polyethylene. Float 304 may be comprised of a reflective material that is less dense than the anesthetic agents to be measured using level sensor 230, enabling float 304 to sit on or at a surface of the liquid anesthetic agent. As one exemplary embodiment, float 304 may be comprised of while nylon. As another exemplary embodiment, float 304 may be comprised of while polypropylene. Further still, in some embodiments, reflectors and/or focusing lenses may be positioned on float 304, such as attached to a top-most surface of float 304.

Level sensor 230 further includes a cap 306 coupled to a bottom portion of measurement tube 302 (with respect to the page and with respect to gravity). In the embodiment shown in FIG. 3, cap 306 interlocks with the bottom-most surface of measurement tube 302, such as by a lip of cap 306 fitting into a groove on measurement tube 302. Furthermore, cap 306 includes a circular central opening, the inner diameter of which is less than the outer diameter of float 304. When the measurement tube is positioned in a sump, as will be elaborated below, the circular central opening may fluidically couple the interior of measurement tube 302 to the interior of the sump. That is, liquid anesthetic agent stored in the sump may enter and exit the bottom of measurement tube 302 via the central opening of cap 306, enabling the liquid anesthetic agent to flow between the interior of measurement tube 302 and the rest of the sump (e.g., exterior to measurement tube 302). Further, the central opening of cap 306 forms a constriction that prevents float 304 from exiting measurement tube 302. Thus, float 304 may sit on or at the surface of the liquid anesthetic agent within measurement tube 302, and the central opening of cap 306 may define the lower bound for the vertical movement of float 304.

Measurement tube 302 may further include one or more vent holes 308 at or near a top of the measurement tube. Vent holes 308 may enable gas transfer (and therefore pressure equalization) between the interior of measurement tube 302 and the exterior of measurement tube 302 (e.g., an interior of the sump), preventing pressure build up or vacuum formation within the interior of measurement tube 302. For example, as will be illustrated in FIG. 8, the vertical position of float 304 changes as the level of liquid anesthetic agent changes. As the level (e.g., height) increases, the vertical position of float 304 increases (e.g., with respect to the z-axis), forcing gas molecules out of measurement tube 302 above float 304 and through vent holes 308 to the exterior of measurement tube 302. That is, the volume above float 304 decreases as float 304 rises within measurement tube 302, and so gas flows out of the interior of measurement tube 302 via vent holes 308 in order to prevent a pressure increase above float 304 that may hinder the vertical movement of float 304. As the level decreases, the vertical position of float 304 decreases, drawing in gas molecules from the exterior of measurement tube 302 via vent holes 308. That is, the volume above float 304 increases and float 304 descends within measurement tube 302, and so gas flows into the interior of measurement tube 302 via vent holes 308 in order to prevent vacuum formation above float 304 and maintain the pressure above float 304 relatively constant. Overall, the pressure equalization helps ensure that when measurement tube 302 is at least partially submerged in the liquid anesthetic agent, the level (e.g., height) of the liquid anesthetic agent within measurement tube 302 is substantially equal to the level of the liquid anesthetic agent exterior to measurement tube 302 within the sump.

Level sensor 230 further includes a retaining bracket 310 coupled to a top portion of measurement tube 302, such as positioned on the top-most surface of measurement tube 302. As shown, retaining bracket 310 may include prongs that extend into the interior of measurement tube 302, each prong having a lip that is shaped to engage with a corresponding opening in measurement tube 302. The engagement of the prongs of retaining bracket 310 with measurement tube 302 fastens (e.g., removably couples) retaining bracket 310 to measurement tube 302. The distance between the prongs across measurement tube 302 is less than the outer diameter of float 304, and thus, the prongs of retaining bracket 310 form a constriction that defines the upper bound for the vertical movement of float 304 within measurement tube 302.

Further, retaining bracket 310 may couple level sensor 230 to a sump (e.g., sump 222 shown in FIG. 2), such as via a plurality of attachment screws 314, and may form a gas-tight seal with the sump via a seal 312 that is coupled within retaining bracket 310. For example, seal 312 may be an elastomeric seal, such as an o-ring, comprised of polytetrafluoroethylene (PTFE), neoprene, polyurethane, or the like that forms a gas-tight barrier between the sump and retaining bracket 310. When level sensor 230 is coupled to the sump, an upper portion of retaining bracket 310 (e.g., the portion of retaining bracket 310 vertically above measurement tube 302) may be external to the sump, whereas a lower portion of retaining bracket 310 (e.g., the portion of retaining bracket 310 within the interior of measurement tube 302) may be located within the interior of the sump. For example, a top wall of a housing of the sump may include an opening that is shaped to receive measurement tube 302 so that measurement tube 302 extends into the interior of the sump. The opening in the sump housing may have an inner diameter that is larger than an outer diameter of measurement tube 302 so that measurement tube 302 can be vertically lowered therein, but small enough that horizontal movement of measurement tube 302 is restricted. Further, the opening in the sump housing may be smaller than a width of the upper portion of retaining bracket 310.

Retaining bracket 310 additionally houses an optical window 318 and an optical sensor 320, which may communicate with a controller (e.g., controller 225 of FIG. 2) via wires 322. In one embodiment, optical sensor 320 is a proximity sensor including at least one light emitter and at least one light detector, as will be further described below with respect to FIG. 4. In other embodiments, optical sensor 320 may be another type of optical sensor that may be used to determine a distance to a measurement target, such as a structured light sensor or a laser Doppler vibrometer.

Optical sensor 320 is positioned to emit light in a top-down manner, toward the interior of measurement tube 302 (e.g., via the at least one light emitter), and receive light from the interior of measurement tube 302 (e.g., via the at least one light emitter). Optical window 318 is shown positioned vertically below optical sensor 320, between optical sensor 320 and the interior of measurement tube 302, and may be comprised of a transparent polymer (e.g., polyphenylsulfone), a crystalline material (e.g., sapphire glass), or another suitable material having high optical transmission in the emission range of the light source and high anesthetic agent compatibility. In some embodiments, optical window 318 may also serve as a focusing lens. Although optical window 318 is shown as a flat window in the example embodiment of FIG. 3, it may be understood that optical window 318 may have various geometries or be configured as various lens types, such as a half-ball lens, a spherical lens, or a Fresnel lens.

Continuing to FIG. 4, a surface view of optical sensor 320 introduced in FIG. 3 is shown. Specifically, FIG. 4 shows an exemplary embodiment of a potential configuration of optical sensor 320, although other configurations are also possible, and includes reference axes 399 introduced in FIG. 3 to show a relative orientation of the views shown in FIGS. 3 and 4. For example, the view of FIG. 4 is in the x-y plane, with the z-axis going into the page. In the embodiment shown in FIG. 4, optical sensor 320 includes a light source 402, an ambient light detector 404, and a light detector 406 within a common housing 408. For example, light source 402 may emit light through a first, light emission aperture in housing 408; ambient light detector 404 may receive and detect light present outside of housing 408 via a second, ambient light sensor aperture in housing 408; and light detector 406 may receive and detect light emitted by light source 402 that has been reflected outside of housing 408 via a third, position return aperture in housing 408. For example, the first aperture may create an illumination cone of a defined geometry for desired illumination properties, and the second and third apertures may create field of view cones of differing defined geometries for desired light collection properties. However, in other embodiments, ambient light detector 404 may not be included. Further, in some such embodiments, light detector 406 may include a filter, such as a bandpass filter, to filter out ambient light that has not been emitted by light source 402.

Light source 402 may emit light of a defined wavelength or wavelength range when commanded (e.g., energized). For example, light source 402 may receive a command signal from controller 225 shown in FIG. 2 via wires 322 shown in FIG. 3. The command signal may include information concerning an intensity of light to emit as well as a duty cycle of activation, for example. In some embodiments, light source 402 may emit light in the near infrared (NIR) or infrared (IR) range. For example, the longer wavelength NIR and IR light may undergo less scattering (compared with shorter wavelength visible light), enabling optical sensor 320 to detect longer distances. In some embodiments, light source 402 may emit light of a defined wavelength within a range between 800 and 950 nanometers (nm). As one exemplary embodiment, light source 402 may be configured to emit 850 nm light. As another exemplary embodiment, light source 402 may be configured to emit 940 nm light. Light source 402 may be a light emitting diode (LED) or a laser, for example.

Ambient light detector 404 may be configured to detect light from a broad wavelength range across the visible spectrum, for example, whereas light detector 406 may be configured to detect light from a narrow wavelength range that includes the wavelength of the light emitted by light source 402. Therefore, light detector 406 may be specifically configured to detect light emitted by light source 402, at least in some embodiments. Further, due to the spacing between light source 402 and light detector 406 and a relatively narrow illumination cone of light source 402 and a relatively narrow field of view cone of light detector 406, light detector 406 may not directly detect light emitted by light source 402. Instead, light detector 406 may detect light emitted by light source 402 that has been reflected, as will be further described below with respect to FIG. 5. One or both of ambient light detector 404 and light detector 406 may be a variable-wavelength detector or a diode array, for example, and may each output a signal (e.g., in volts or amps) based on characteristics of the light received. For example, as the intensity of light received increases, the voltage output of ambient light detector 404 or light detector 406 may increase. The signals output by ambient light detector 404 and light detector 406 may be received by the controller, which may perform various data processing actions, as further described herein.

Figure 5:
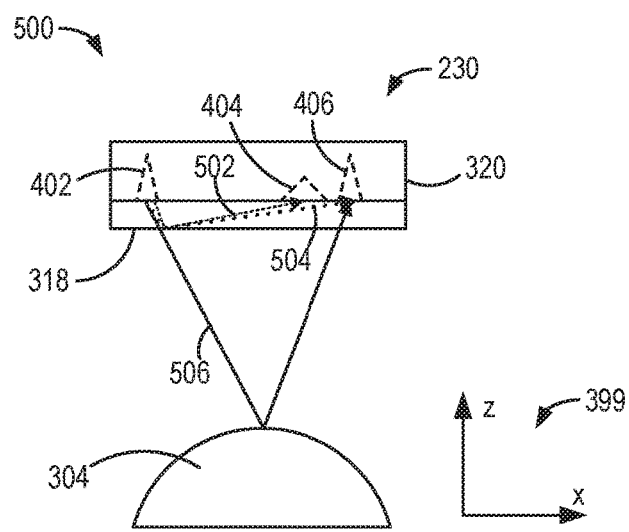
FIG. 5 shows a diagram of light emission and light detection by a time-of-flight proximity sensor included in an optical level sensor for determining an anesthetic agent volume.

Continuing to FIG. 5, a diagram 500 illustrates light emission and light detection by optical sensor 320 of level sensor 230. As such, components previously introduced in FIGS. 2-4 are numbered the same and may not be reintroduced. FIG. 5 includes reference axes 399 to highlight the relative arrangement of components with respect to the views shown in FIGS. 3 and 4. For example, the view of FIG. 5 is in the x-z plane, with the y-axis going into the page. Further, a simplified view of level sensor 230 is shown, without all of the components included, although it may be understood that such components may be present (e.g., measurement tube 302).

Diagram 500 shows a partial side view of level sensor 230, including optical sensor 320 positioned directly above and in face-sharing contact with optical window 318. Optical window 318 covers light source 412, ambient light detector 404, and light detector 406, the positions of which are schematically illustrated by dashed lines. Float 304 is partially shown a distance below (and not in direct contact with) optical window 318.

In general, optical sensor 320 may be used to determine a travel time of a photon of light from an emitter (e.g., light source 402) to a detector (e.g., either ambient light detector 404 or light detector 406), which directly relates to a travel distance of the photon of light. As will be elaborated below, light emitted by light source 402 may be at least partially reflected by a target (e.g., float 304) and directed back toward optical sensor 320. A time delay between light emission by light source 402 and light detection by light detector 406 may be determined as a travel time of the photon of light. Because the speed of light is a known constant, the travel time multiplied by the speed of light is equivalent to the distance which the photon of light has traveled. As a non-limiting illustrative example, 1 cm of distance between optical sensor 320 and a reflector may result in a 66 psec travel time. Furthermore, the travel time is not affected by target reflectance, although high reflectivity may increase an amount (or intensity) of light that is reflected.

Light emitted by light source 402 is directed downward toward optical window 318. Because optical window 318 is transparent, at least a portion of the light emitted by light source 402 passes through optical window 318, while a portion may be reflected by the optical window (e.g., at a window/gas interface). Light source 402 may be activated to emit light in pulses, each pulse having a predetermined duration and with a predetermined interval between each pulse. For example, controller 225 (not shown in FIG. 5) may command light source 402 at a predetermined duty cycle of activation according to instructions stored in memory. As an illustrative example, diagram 500 shows light paths for three different photons of light emitted by light source 402, including light path 502, light path 504, and light path 506.

Light in light path 502 is reflected by optical window 318 and received by ambient light detector 404, which may also receive any ambient light present. Although measurement tube 302 (not shown in FIG. 5) and its position within sump 222 (also not shown in FIG. 5) may reduce ambient light exposure, ambient light detector 404 enables compensation for optical crosstalk and high ambient light conditions as well as light distortions made by optical window 318. For example, the controller may receive a signal output from ambient light detector 404, which may correspond to an intensity of all light (including light in light path 502 in addition to any ambient light), and use the signal output from ambient light detector 404 to adjust distance calculations made using measurements received from light detector 406 according to instructions stored in memory. As one example, because light source 402 may emit light in pulses and ambient light may remain relatively constant, the controller may determine an intensity of ambient light present based on a relatively constant signal component received from ambient light sensor 404. Further, the controller may subtract the determined intensity of the ambient light from a signal output by light detector 406. In a further embodiment, an optically opaque feature can be disposed within the optical window and between light source 402 and light detector 406, thereby forming individual windows (e.g., one window for the emitter, one for the detector) to prevent and/or reduce optical crosstalk.

Light in light path 504 is reflected by optical window 318 (e.g., at the window/gas interface) and is received by light detector 406. However, because optical window 318 is a fixed, known distance from light detector 406, the controller may identify signals output by light detector 406 that correspond to reflections by optical window 318. In contrast, float 304 is a variable distance from light source 402 and light detector 406. Light in light path 506 is reflected by float 304 and received by light detector 406. An elapsed time between light source 402 emitting light and light detector 406 receiving light reflected by float 304 (e.g., in light path 506) changes based on the distance between float 304 and optical sensor 320. For example, as the distance between float 304 and optical sensor 320 increases, the elapsed time increases, and as the distance between float 304 and optical sensor 320 decreases, the elapsed time decreases. The controller may receive a signal output by light detector 406 (e.g., via wires 322 shown in FIG. 3) that directly corresponds to the distance between float 304, and thus the surface of liquid anesthetic agent within the measurement tube, and optical sensor 320. For example, the controller may include a look-up table, graph, or function stored in memory that relates the signal output of light detector 406 to a distance between float 304 and optical sensor 320 and takes into account sensor calibrations (to account for distortions by optical window 318, a height of float 304 above the liquid level, etc.). In an alternative embodiment, the signal output by light detector 406 may correspond to the elapsed time, and the controller may calculate the distance to the surface of liquid anesthetic agent within measurement tube 302 based on the elapsed time and the speed of light, as mentioned above, according to instructions stored in memory, which may also take into account sensor calibrations.

FIG. 6 illustrates an example graph 600 of a relationship between a measurement sample number made by a level sensor (e.g., level sensor 230 described with respect to FIGS. 2-5) and a liquid surface distance from the level sensor. The measurement sample number is shown on the horizontal axis, with the measurement sample number increasing from left to right and increasing with time. For example, each measurement sample may refer to a discrete measurement made by the level sensor, such as one light pulse emission by light source 402 and the corresponding detection by light detector 406, each introduced in FIG. 4. The vertical axis shows the liquid surface distance from the level sensor, with the liquid surface distance increasing along the vertical axis from bottom to top. In the example of graph 600, the liquid surface is a surface of liquid anesthetic agent within a sump of an anesthetic vaporizer, such as according to the system shown in FIG. 2.

Graph 600 includes a plot 602 showing how the liquid surface distance from the sensor changes as the sump is emptied over a measurement period lasting from the lowest measurement sample number to the highest measurement sample number. Graph 600 also includes a first bound 604, corresponding to a smallest liquid surface distance from the sensor that the sensor can measure, and a second bound 606, corresponding to a largest surface distance from the sensor that the sensor can measure. For example, the first bound 604 and the second bound 606 may be defined by physical constraints of the level sensor, such as the constrictions described above with respect to FIG. 3 that define bounds for vertical moment of a measurement target (e.g., float 304) within a measurement tube (e.g., measurement tube 302).

The sump is completely full at the beginning of the measurement period (e.g., the first measurement sample). As a result, the float is the closest it can get to the level sensor, and so the liquid surface distance from the sensor measured by the level sensor (plot 602) is equal to the first bound 604. As the sump is drained over the measurement period, the measured liquid surface distance from the sensor (plot 602) increases, corresponding to a decrease in the level (and volume) of liquid anesthetic agent in the sump. The measured liquid surface distance from the sensor (plot 602) approaches the second bound 606 near the end of the measurement period and reaches the second bound 606 at the last measurement sample. For example, the float is the furthest it can get from the level sensor, and thus, even if the liquid level were to continue to decrease, the level sensor may not detect these changes.

Further, a controller (e.g., controller 225 of FIG. 2) may use the measured liquid surface distance from the sensor to determine a liquid volume in the sump according to a pre-calibrated relationship stored in memory. Continuing to FIG. 7, an example graph 700 shows a plot 702 of an inverse linear relationship between the measured liquid surface distance from the sensor and the liquid volume in the sump. Graph 700 includes the measured liquid surface distance from the sensor as the horizontal axis, with the distance increasing along the horizontal axis from left to right, and the liquid volume in the sump as the vertical axis, with the liquid volume increasing up the vertical axis from bottom to top.

Plot 702 shows that as the measured liquid surface distance from the sensor increases, the volume of the liquid anesthetic agent in the sump decreases. Further, plot 702 is bounded by a lower bound 704, corresponding to a lowest volume that the sensor can measure, and an upper bound 706, corresponding to a highest volume that the sensor can measure. For example, lower bound 704 may correspond to second bound 606 of FIG. 6, representing a first, lower volume of liquid anesthetic agent in the sump when the float reaches its lowest possible position in the measurement tube. Upper bound 706 may correspond to first bound 604 of FIG. 6, representing a second, higher volume of liquid anesthetic agent in the sump when the float reaches its highest possible position in the measurement tube. Both lower bound 704 and upper bound 706 may be pre-calibrated values that may change based on a size (e.g., capacity) and geometry of the sump.

In one embodiment, the controller may reference graph 700 to determine the liquid volume in the sump, such as by determining a corresponding liquid volume for a received measured liquid surface distance from the sensor using plot 702. In another embodiment, the controller may additionally or alternatively refer to a look-up table of values that define plot 702. For example, the controller may input the measured liquid surface distance from the sensor into the look-up table, which may output the corresponding liquid volume in the sump. In still another embodiment, the controller may additionally or alternatively determine the liquid volume in the sump as a function of the measured surface distance from the sensor. For example, the controller may input the measured liquid surface distance from the sensor into an equation that defines the relationship shown in plot 702, which may output the corresponding liquid volume in the sump.

Next, FIG. 8 schematically shows an example timeline 800 illustrating usage of an optical ToF proximity sensor for determining an anesthetic agent level in an anesthetic vaporizer. The anesthetic vaporizer may be anesthetic vaporizer 200 introduced in FIG. 2, including level sensor 230 coupled in sump 222. As such, components of FIG. 8 that function the same as components previously introduced in FIGS. 2 and 3 are numbered the same and may not be reintroduced. Further, some components of anesthetic vaporizer 200 and level sensor 230 are not shown in the example of timeline 800 for simplicity, although it may be understood that such components are present. Controller 225 (not shown in FIG. 8) may execute one or more methods to determine a volume of the liquid anesthetic agent 210 within sump 222 based on data received from level sensor 230, such as the example method described below with respect to FIG. 9.

Timeline 800 shows a plurality of "snapshots," each representing an instantaneous depiction of an amount (e.g., volume) of liquid anesthetic agent 210 within sump 222 at the corresponding time, including a first snapshot 802 at a first time t1, a second snapshot 804 at a second time t2, a third snapshot 806 at a third time t3, and a fourth snapshot 808 at a fourth time t4. The first time is the earliest time and the fourth time is the latest time, as shown by a direction of a time axis 801. In particular, each snapshot shows how float 304 vertically moves with a changing level of liquid anesthetic agent 210 within sump 222 (and therefore within measurement tube 302) and the resulting changes in the distance to float 304 measured by optical sensor 320.

First snapshot 802 shows float 304 at a first distance d1 from optical sensor 320. Further, float 304 is between a minimum level 810 (e.g., corresponding to a maximum possible distance between optical sensor 320 and float 304, such as corresponding to second bound 606 of FIG. 6) and a maximum level 812 (e.g., corresponding to a minimum possible distance between optical sensor 320 and float 304, such as corresponding to first bound 604 of FIG. 6). For example, a top-most surface of float 304 cannot drop below the minimum level 810 due to a restriction at the bottom of measurement tube 302. Similarly, due to a restriction near the top of measurement tube 302, the top-most surface of float 304 cannot rise above the maximum level 812, creating a "dead space" at the top of the tube. Thus, only liquid levels between the minimum level 810 and the maximum level 812 (e.g., greater than the minimum level 810 and less than the maximum level 812) result in accurate liquid level measurements by optical sensor 320. Because the first distance d1 is between the minimum level 810 and the maximum level 612, the controller accurately calculates the volume of liquid anesthetic agent 210 as a first volume V1 based on the first distance measurement received from optical sensor 320, such as by inputting d1 into one or more pre-calibrated look-up tables, equations, or graphs, such as graph 700 described above with respect to FIG. 7.

Between time t1 and time t2, the anesthetic vaporizer is operated to deliver anesthetic agent to a patient. As shown in second snapshot 804, a vertical height of the float 304 decreases with the vertical height of liquid anesthetic agent 210 within measurement tube 302 and external to measurement tube 302. Float 304 has a second distance d2 from optical sensor 320, which is greater than first distance d1 at time t1. The second distance d2 remains between the minimum level 810 and the maximum level 612, and so the controller accurately calculates the volume of liquid anesthetic agent 210 as a second volume V2, which is less than V1, based on the second distance measurement received from optical sensor 320.

The anesthetic vaporizer continues to be operated between time t2 and time t3. Third snapshot 806 shows float 304 having a third distance d3 from optical sensor 320, which is greater than each of first distance d1 and second distance d2. Further, the level of liquid anesthetic agent 210 in sump 222 has decreased below minimum level 810, and measurement tube 302 is no longer at least partially submerged within liquid anesthetic agent 210. Therefore, the controller is unable to accurately calculate a third volume V3 based on the third distance measurement received from optical sensor 320, but may recognize that float 304 has reached the minimum level 810 based on the measured third distance d3. In some embodiments, the controller may take an action, such as outputting an alert to refill the sump, responsive to measuring third distance d3.

Sump 222 is refilled between time t3 and time t4. As shown in fourth snapshot 808, a vertical height of the float 304 increases due to the refilled liquid anesthetic agent 210. Float 304 has a fourth distance d4 from optical sensor 320, which is the smallest distance shown in timeline 800 and remains between the minimum level 810 and the maximum level 612. The controller accurately calculates the volume of liquid anesthetic agent 210 as a fourth volume V4, which is the greatest volume shown in timeline 800, based on the fourth distance measurement received from optical sensor 320. In some embodiments, the controller may provide real-time filling information via a display of a human-machine interface (e.g., HMI 226 of FIG. 2) to indicate the level of filling based on the signal received from optical sensor 230 during refilling. This feature can be used to prevent an unintended potential overfill/overflow of the liquid anesthetic by alerting a user and/or closing a valve which fluidically couples an inlet filler port to the sump. For example, the controller may output the real-time volume (or level) of liquid anesthetic agent 210, as determined via level sensor 230, via the HMI and may further output an overfill alert and/or actuate the inlet filler port valve closed responsive to the volume (or level) surpassing a maximum volume (or level).

Figure 9:
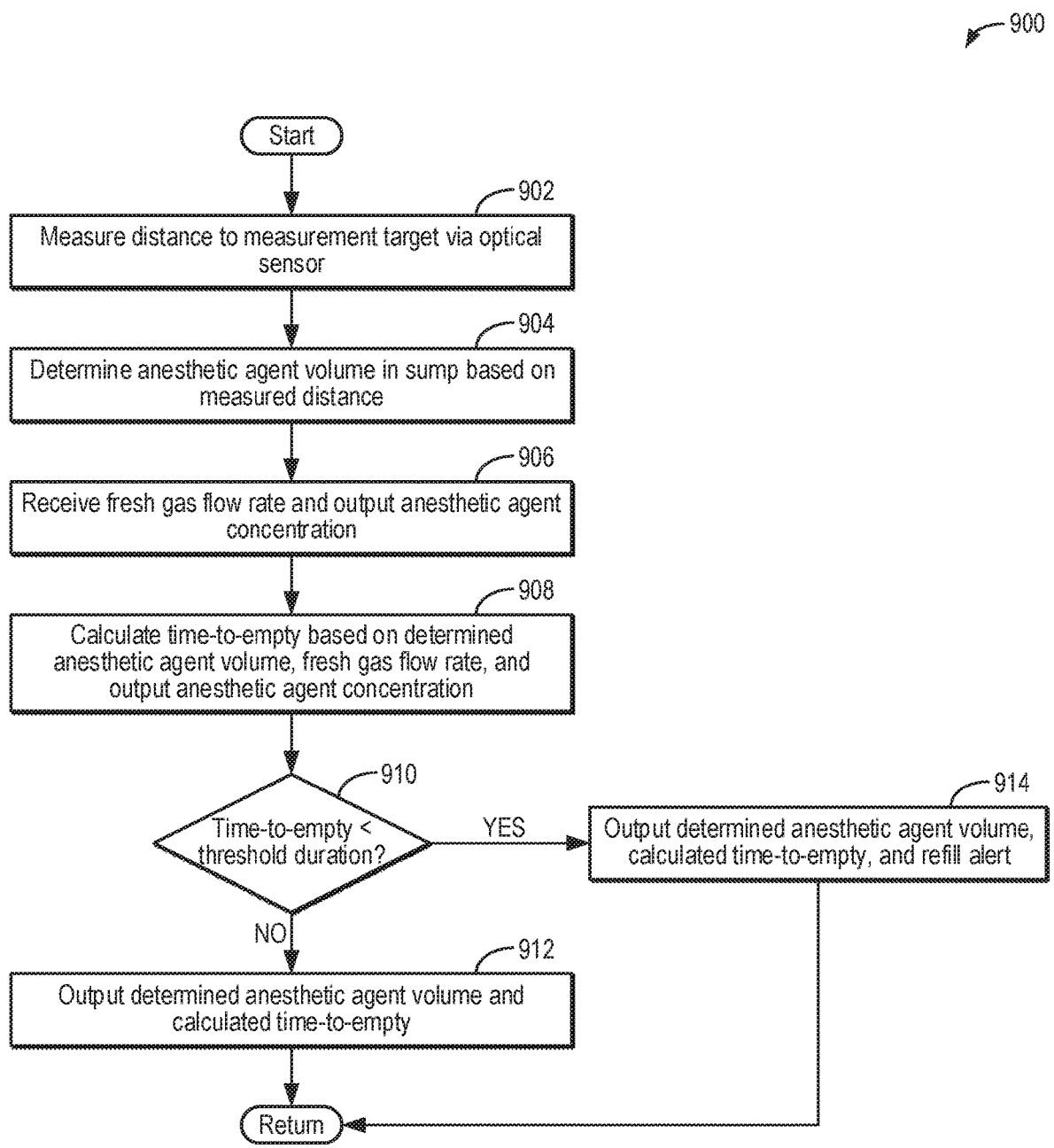
FIG. 9 is a flow chart illustrating an exemplary embodiment of a method for determining a time-to-empty of an anesthetic vaporizer sump based on measurements made by an optical level sensor.

Turning now to FIG. 9, a high-level flow chart of an example method 900 for determining a volume of liquid anesthetic agent in an anesthetic vaporizer sump using a level sensor is shown. Method 900 may be executed by a controller, such as controller 225 of FIG. 2, according to instructions stored in a memory of the controller (e.g., memory 228 of FIG. 2) and in conjunction with one or more inputs, such as inputs received from an operator via a human-machine interface (e.g., HMI 226 of FIG. 2) and one or more sensors (e.g., level sensor 230 introduced in FIG. 2). Further, the controller may output information to the operator of the anesthesia machine via the human-machine interface. Although method 900 will be described with respect to anesthetic vaporizer 200 shown in FIG. 2, it may be understood that method 900 may be applied to any anesthetic vaporizer configuration that includes an electronic controller and a level sensor that uses time-of-flight sensing.

A distance to a measurement target is measured via an optical sensor at 902. The optical sensor is the proximity sensing component of the level sensor (e.g., optical sensor 320 introduced in FIG. 3), and the measurement target may be a reflective float (e.g., float 304 introduced in FIG. 3) positioned within a non-reflective measurement tube (e.g., measurement tube 302 introduced in FIG. 3). Measuring the distance to the measurement target via the optical sensor may include operating a light source of the optical sensor (e.g., light source 402 shown in FIGS. 4-5) to emit pulses of light at a predetermined duty cycle of operation and measuring an elapsed time between the emission of each pulse and light detection by a light detector (e.g., light detector 406 shown in FIGS. 4-5). The optical sensor may output a signal to the controller corresponding to the distance and/or corresponding to the elapsed time, as elaborated above with respect to FIG. 5.

An anesthetic agent volume in the sump is determined based on the measured distance at 904. The controller may store a pre-calibrated relationship between the measured distance and the anesthetic agent volume in memory, such as stored as a graph, look-up table, or equation. Therefore, the controller may input the measured distance into the graph, look-up table, or equation, which may output the corresponding anesthetic agent volume that produces the measured distance. As mentioned above with respect to FIG. 7, the pre-calibrated relationship may be specific to each sump configuration (e.g., volume capacity and/or geometry). As one example, smaller volume changes may result in larger distance changes between the optical sensor and the measurement target when the sump is narrower and taller compared to when the sump is wider and shorter for a same volume capacity.

A fresh gas flow rate and an output anesthetic agent concentration are received at 906. For example, the controller may receive a measurement of a concentration of anesthetic agent output by the anesthetic vaporizer from a concentration sensor (e.g., concentration sensor 256 of FIG. 2) and a fresh gas flow rate measurement indicative of the flow rate of the fresh gas into the anesthetic vaporizer from a mass flow sensor (e.g., first mass flow sensor 241). Alternatively, the controller may receive an output anesthetic agent concentration setpoint and a fresh gas flow rate setpoint from the operator via the human-machine interface. For example, the controller may use the setpoints when measured values are unavailable.

A time-to-empty is calculated based on the determined anesthetic agent volume (e.g., as determined at 904), the fresh gas flow rate, and the output anesthetic agent concentration at 908. The time-to-empty refers to a remaining time duration until the volume liquid anesthetic agent in the sump is depleted. Additionally or alternatively, the time-to-empty refers to a remaining operational time of the anesthetic vaporizer using the current operating conditions. In one embodiment, the time-to-empty may correspond to the remaining time duration until the volume of liquid anesthetic reaches zero (e.g., the sump is completely empty). In another embodiment, the time-to-empty may correspond to the remaining time duration until the volume of liquid anesthetic reaches a non-zero volume, such as a lowest measureable volume by the level sensor.

In one embodiment, the controller may calculate the time-to-empty based on a running average the fresh gas flow rate (e.g., over a predetermined duration of anesthetic agent usage, such as a duration in a range from 1 to 5 minutes), a running average of the output anesthetic agent concentration (e.g., over the duration), and the determined anesthetic agent volume in the sump into one or more look-up tables, graphs, or equations. As one example, the controller may calculate the time-to-empty using the following equations:

$$\text{Saturated\_Gas\_Volume} = \frac{SW \cdot GC \cdot (273 + T)}{MW \cdot 273} \quad \text{(Equation 1)}$$

$$\text{Time\_to\_Empty} = \frac{\text{Volume\_in\_Sump} \times \text{Saturated\_Gas\_Volume} \times 100}{\text{Ave\_FGF} \times \text{Ave\_Agent\_Conc}} \quad \text{(Equation 2)}$$

Equation 1 results in the term Saturated_Gas_Volume (in milliliters, mL), which corresponds to an amount of vaporized anesthetic agent produced at a given temperature (T) of the anesthetic agent for the type of anesthetic agent being used. The term SW is the specific weight of the anesthetic agent in g/mL, which is selected based on the type of anesthetic agent being used (e.g., 1.49 g/mL for isoflurane, 1.53 g/mL for sevoflurane, or 1.47 g/mL for desflurane). For example, the controller may input the type of anesthetic agent into a look-up table, which may output the specific weight of the given type of anesthetic agent. The term GC is Avogadro's gas constant, which is a universal constant for all gases (e.g., independent of the type of anesthetic agent being used) that defines that at standard conditions for temperature and pressure, dry (e.g., STPD, corresponding to a temperature of 273 K and a pressure of 1 atmosphere, without water vapor), one mole of any gas contains $6.022 \times 10^{23}$ molecules, which occupy a volume of 22,400 mL. The term MW is the molecular weight of the anesthetic agent being used in g/mol, which is selected based on the type of anesthetic agent being used (e.g., 184 g/mol for isoflurane, 200 g/mol for sevoflurane, or 168 g/mol for desflurane). For example, the controller may input the type of anesthetic agent into a separate look-up table, which may output the molecular weight of the given type of anesthetic agent.

The Saturated_Gas_Volume calculated via Equation 1 may be used in Equation 2 to determine Time_to_Empty (in minutes), which corresponds to the duration of time remaining before the sump is emptied at the current anesthetic agent usage rate. In Equation 2, the term Ave_FGF is the average fresh gas flow rate (in mL/min), the term Ave_Agent_Conc is the average output anesthetic agent concentration (in % volume), and the term Volume_in_Sump is the anesthetic agent volume determined via the optical sensor (e.g., at 904).

It is determined if the time-to-empty is less than a threshold duration at 910. The threshold duration may be a non-zero time duration corresponding to a remaining time of anesthetic agent usage below which refilling the sump is indicated. For example, the threshold duration may provide a time buffer to account for an anticipated amount of time it may take the operator to refill the sump, thereby reducing instances of the sump becoming completely empty (or reaching a non-zero minimum volume).

If the time-to-empty is not less than the threshold duration, method 900 proceeds to 912, and the determined anesthetic agent volume and the calculated time-to-empty are output. For example, the controller may output the determined anesthetic agent volume (e.g., determined at 904) and the calculated time-to-empty (e.g., calculated at 908) via the human-machine interface, such as via one or more of a visual and an audible message. Method 900 may then return so that the anesthetic agent volume and the time-to-empty may be updated as new measurements are made by the optical sensor.

If the time-to-empty is less than the threshold duration, method 900 proceeds to 914, and the determined anesthetic agent volume, the calculated time-to-empty, and a refill alert are output. For example, in addition to outputting the determined anesthetic agent volume and the calculated time-to-empty, as described above at 912, the controller may communicate the refill alert via the human-machine interface. In one embodiment, the refill alert may include an audible alarm or message. In another embodiment, the refill alert may additionally or alternatively include a visual message. Method 900 may then return.

Thus, the systems and methods described herein provide for determining and tracking a volume of an anesthetic agent in a sump of an anesthetic vaporizer. As a result, refill alerts may be output prior to the sump reaching an empty status. Further, by determining the volume via an optical sensor that uses a top-down time-of-flight measurement, the measurement will not be impacted by characteristics of the anesthetic agent, which may change over time (due to a reactivity of the anesthetic agent, a temperature of the anesthetic agent, humidity, etc.). A technical effect of determining a volume of liquid anesthetic via an optical time-of-flight sensor is that an accuracy of the determined volume may be increased.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for an anesthetic vaporizer comprising:
a sump configured to hold a liquid anesthetic agent;
a measurement tube including a float positioned therein, a bottom portion of the measurement tube coupled to a cap having a central opening;
a retaining bracket coupled to a top portion surface of the measurement tube;
an optical sensor housed within the retaining bracket, the optical sensor including a light source positioned to emit light toward an interior of the measurement tube and a light detector positioned to receive light from the interior of the measurement tube; and
an optical window housed within the retaining bracket and coupled between the optical sensor and the interior of the measurement tube,
wherein the retaining bracket couples the optical sensor to the sump of the anesthetic vaporizer, the retaining bracket being positioned on an exterior of the sump and the measurement tube being positioned within the sump, wherein the retaining bracket includes a seal coupled therein, the seal forming a gas-tight barrier between the sump and the retaining bracket.

2. The system of claim 1, wherein the measurement tube is an elongated hollow cylinder comprised of a non-reflective material, the float is a sphere comprised of a reflective material, and an inner diameter of the central opening of the cap is less than an outer diameter of the float.

3. The system of claim 1, wherein the float is configured to have a lower density than a liquid anesthetic agent stored in the sump, and a vertical position of the float is configured to change based on a height of the liquid anesthetic agent within the sump.

4. The system of claim 1, wherein a level sensor outputs a signal corresponding to a transit time of light emitted by the light source, reflected by the float, and received by the light detector.

5. The system of claim 1, wherein the float is comprised of at least one of nylon and polypropylene.

6. The system of claim 1, wherein the measurement tube is comprised of at least one of black nickel-plated aluminum and polypropylene.

7. The system of claim 1, wherein the optical window is comprised of at least one of polyphenylsulfone and sapphire glass.

8. A system for an anesthetic vaporizer, comprising:
a sump configured to hold a liquid anesthetic agent;
a level sensor including a retaining bracket coupled to a top exterior surface of the sump, a measurement tube extending from the retaining bracket into the interior of the sump and configured to be at least partially submerged in the liquid anesthetic agent, a float positioned within the measurement tube, and an optical sensor coupled within the retaining bracket vertically above the measurement tube, wherein the retaining bracket includes a seal coupled therein, the seal forming a gas-tight barrier between the sump and the retaining bracket; and
a controller storing executable instructions in non-transitory memory that, when executed, cause the controller to:
operate the level sensor to measure a distance between the optical sensor and the float;
calculate a current volume of the liquid anesthetic agent in the sump and a remaining time until the sump is empty based on the distance measured by the level sensor; and
output a refill alert responsive to the remaining time decreasing below a threshold.

9. The system of claim 8, wherein the optical sensor includes a light source configured to emit light of a defined wavelength in a range between 800 and 950 nanometers toward the float and a light detector configured to receiving the light of the defined wavelength that is reflected by the float, and wherein to operate the level sensor to measure the distance between the optical sensor and the float, the controller includes further instructions stored in non-transitory memory that, when executed, cause the controller to:
activate the light source to emit a pulse of light;
determine an elapsed time between emitting the pulse of light and receiving the light at the detector; and
determine the distance between the optical sensor and the float based on the elapsed time.

10. The system of claim 8, wherein an outer diameter of the float is smaller than an inner diameter of the measurement tube, and the float is less dense than the liquid anesthetic agent.

11. The system of claim 10, wherein a vertical movement of the float within the measurement tube is constrained by a cap on a bottom-most surface of the measurement tube, the cap having an opening with a smaller inner diameter than the outer diameter of the float, and prongs of the retaining bracket that extend into a top portion of the measurement tube, a width between the prongs smaller than the outer diameter of the float, and wherein the measurement tube does not contact a bottom inner surface of the sump.

12. The system of claim 8, wherein the sump includes a filler port with an inlet filler port valve coupled therein, and wherein the controller includes further instructions stored in non-transitory memory that, when executed during refilling of the sump, cause the controller to:
output an overfill alert and actuate closed the inlet filler port valve responsive to the current volume surpassing a maximum volume.

13. The system of claim 8, wherein the level sensor further includes a light source, a light detector, and an ambient light detector,
wherein the controller includes further instructions stored in non-transitory memory that, when executed, cause the controller to:
determine an intensity of ambient light based on an output of the ambient light detector; and
subtract the determined intensity of ambient light from a signal output by the light detector.

14. The system of claim 8, wherein the level sensor further includes a light source, a light detector, and an optical window housed within the retaining bracket and coupled between the optical sensor and the interior of the measurement tube,
wherein the controller includes further instructions stored in non-transitory memory that, when executed, cause the controller to identify signals output by the light detector that correspond to reflections by the optical window.

* * * * *